US00PP18352P2

(12) United States Plant Patent
Hansen

(10) Patent No.: US PP18,352 P2
(45) Date of Patent: Dec. 25, 2007

(54) ***CLEMATIS* PLANT NAMED 'ICE CRYSTAL'**

(50) Latin Name: *Clematis hybrida*
Varietal Denomination: Ice Crystal

(75) Inventor: Flemming Hansen, Ronde (DK)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/494,094

(22) Filed: Jul. 27, 2006

(51) Int. Cl.
*A01H 5/00* (2006.01)

(52) U.S. Cl. ..... Plt./228

(58) Field of Classification Search ..... Plt./228
See application file for complete search history.

*Primary Examiner*—Kent L. Bell
(74) *Attorney, Agent, or Firm*—C. A. Whealy

(57) ABSTRACT

A new and distinct cultivar of *Clematis* plant named 'Ice Crystal', characterized by its vining plant habit; freely flowering habit; and large light violet blue-colored flowers.

2 Drawing Sheets

Botanical designation: *Clematis hybrida.*
Cultivar denomination: 'Ice Crystal'.

BACKGROUND OF THE INVENTION

The present invention relates to a new and distinct cultivar of *Clematis,* botanically known as *Clematis hybrida* and hereinafter referred to by the name 'Ice Crystal'.

The new *Clematis* originated from an open-pollination of an unnamed selection of *Clematis hybrida,* not patented, as the female, or seed, parent with an unknown selection of *Clematis hybrida,* as the male, or pollen, parent. The new *Clematis* was discovered and selected by the Inventor as a single flowering plant from within the progeny of the stated open-pollination grown in a controlled environment in Ugelbolle, Denmark in 2001.

Asexual reproduction of the new cultivar by softwood cuttings in Ugelbolle, Denmark, since 2002, has shown that the unique features of this new *Clematis* are stable and reproduced true to type in successive generations.

SUMMARY OF THE INVENTION

Plants of the cultivar Ice Crystal have not been observed under all possible environmental conditions. The phenotype may vary somewhat with variations in environment such as temperature and light intensity without, however, any variance in genotype.

The following traits have been repeatedly observed and are determined to be the unique characteristics of 'Ice Crystal'. These characteristics in combination distinguish 'Ice Crystal' as a new and distinct cultivar:

1. Vining plant habit.
2. Freely flowering habit.
3. Large light violet blue-colored flowers.

Plants of the new *Clematis* differ from plants of the female parent selection primarily in flower size and color.

Plants of the new *Clematis* can be compared to plants of the *Clematis* cultivar Multi Blue, not patented. In side-by-side comparisons conducted by the Inventor in Ugelbolle, Denmark, plants of the new *Clematis* differed primarily from plants of the cultivar Multi Blue in flower color as plants of the cultivar Multi Blue had darker violet blue-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Clematis.*

The photograph on the first sheet comprises a side perspective view of typical flowering plants of 'Ice Crystal' grown in a container.

The photograph at the top of the second sheet is a close-up view of a typical flower of 'Ice Crystal'.

The photograph at the bottom of the second sheet is a close-up view of a typical leaf of 'Ice Crystal'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photograph and following description were grown under conditions which closely approximate commercial production conditions during the summer in an outdoor nursery in Lisserbroek, The Netherlands for about one year. During the production of the plants, day temperatures ranged from 14° C. to 32° C. and night temperatures ranged from 7° C. to 14° C.

Botanical classification: *Clematis hybrida* cultivar Ice Crystal.

Parentage:

*Female parent.*—Unnamed selection of *Clematis hybrida,* not patented.

*Male parent.*—Unknown selection of *Clematis hybrida,* not patented.

Propagation:

*Type cutting.*—Softwood cuttings.

*Time to initiate roots.*—About 20 to 30 days at 18° C.

*Time to produce a rooted young plant.*—About 100 days at 22° C.

*Root description.*—Moderately fine, fibrous, moderately fleshy; light brown to white in color.

*Rooting habit.*—Moderately freely branching; moderately dense.

Plant description:

*Form.*—Perennial. Vining plant habit; basal branching habit. Moderately vigorous growth habit. Large single flowers.

*Plant height.*—About 64 cm.

*Plant width.*—About 20 cm.

*Lateral branch description.*—Length: About 64 cm. Diameter: About 2 cm. Internode length: About 11.1 cm. Strength: Strong. Aspect: Upright. Texture: Pubescent. Color: 200B.

Foliage description:

*Arrangement.*—Opposite, compound with three leaflets.

*Length, leaf.*—About 10.2 cm.

*Length, terminal leaflet.*—About 7 cm.

*Length, lateral leaflets.*—About 6.1 cm.

*Width, leaf.*—About 11.8 cm.

*Width, terminal leaflet.*—About 5.1 cm.

*Width, lateral leaflets.*—About 3.5 cm.

*Shape, leaflets.*—Ovate.

*Apex, leaflets.*—Acute.

*Base, leaflets.*—Rounded to cordate.

*Margin, leaflets.*—Entire.

*Texture, leaflets, upper and lower surfaces.*—Smooth, glabrous.

*Venation pattern, leaflets.*—Pinnate.

*Color, leaflets.*—Developing foliage, upper surface: 137A. Developing foliage, lower surface: 137D. Fully expanded foliage, upper surface: Between 137A and 139A; venation, 138A to 138B. Fully expanded foliage, lower surface: 138A; venation, 143A.

*Petiole length.*—About 8.1 cm.

*Petiole diameter.*—About 1 mm.

*Petiole color, upper surface.*—200B.

*Petiole color, lower surface.*—143A.

Flower description:

*Flower arrangement and shape.*—Large single terminal and axillary flowers; flowers face upright to slightly outward. Freely flowering, at one time, about six open flowers and flower buds per lateral branch.

*Natural flowering season.*—Continuous flowering from early June to September in The Netherlands.

*Flower longevity on the plant.*—About ten days; flowers not persistent.

*Fragrance.*—None detected.

*Flower buds.*—Length: About 2.4 cm. Diameter: About 1.3 cm. Shape: Ovate. Color: 145A with longitudinal stripes, 145D.

*Flowers.*—Diameter: About 9.9 cm. Depth (height): About 1.6 cm.

*Petals.*—Arrangement: Six in a single whorl. Length: About 5.1 cm. Width: About 2.8 cm. Shape: Broadly elliptical. Apex: Acute. Margin: Entire; undulate. Texture, upper and lower surfaces: Smooth, glabrous. Color: When opening, upper and lower surfaces: Center and towards the base, 155A; towards the margins, 91B to 91C; at the margins, 91A. Fully opened, upper and lower surfaces: Center and towards the base, 155A; towards the margins, 92B to 92C; at the margins, 92A.

*Sepals.*—Sepal development has not been observed.

*Peduncles.*—Length: About 9.2 cm. Diameter: About 2 mm. Aspect: About 45° from vertical. Strength: Strong. Texture: Smooth, glabrous. Color: 143B.

*Reproductive organs.*—Stamens: Quantity per flower: About 50. Anther shape: Linear. Anther length: About 4 mm. Anther color: 5D. Filament length: About 1 cm. Filament color: 155C. Pollen amount: Scarce. Pollen color: 5D. Pistils: Quantity per flower: About 60. Pistil length: About 9 mm. Stigma shape: Conical, narrow. Stigma color: 157A to 157B. Style length: About 6 mm. Style color: Lighter than 146D. Ovary color: 157A.

*Seed/fruit.*—Seed and fruit production has not been observed.

Disease/pest resistance: Plants of the new *Clematis* have not been noted to be resistant to pathogens and pests common to *Clematis.*

Garden performance: Plants of the new *Clematis* have exhibited good tolerance to rain and wind and have been observed to be suitable for USDA Zones 6 to 9.

It is claimed:

1. A new and distinct *Clematis* plant named 'Ice Crystal' as illustrated and described.

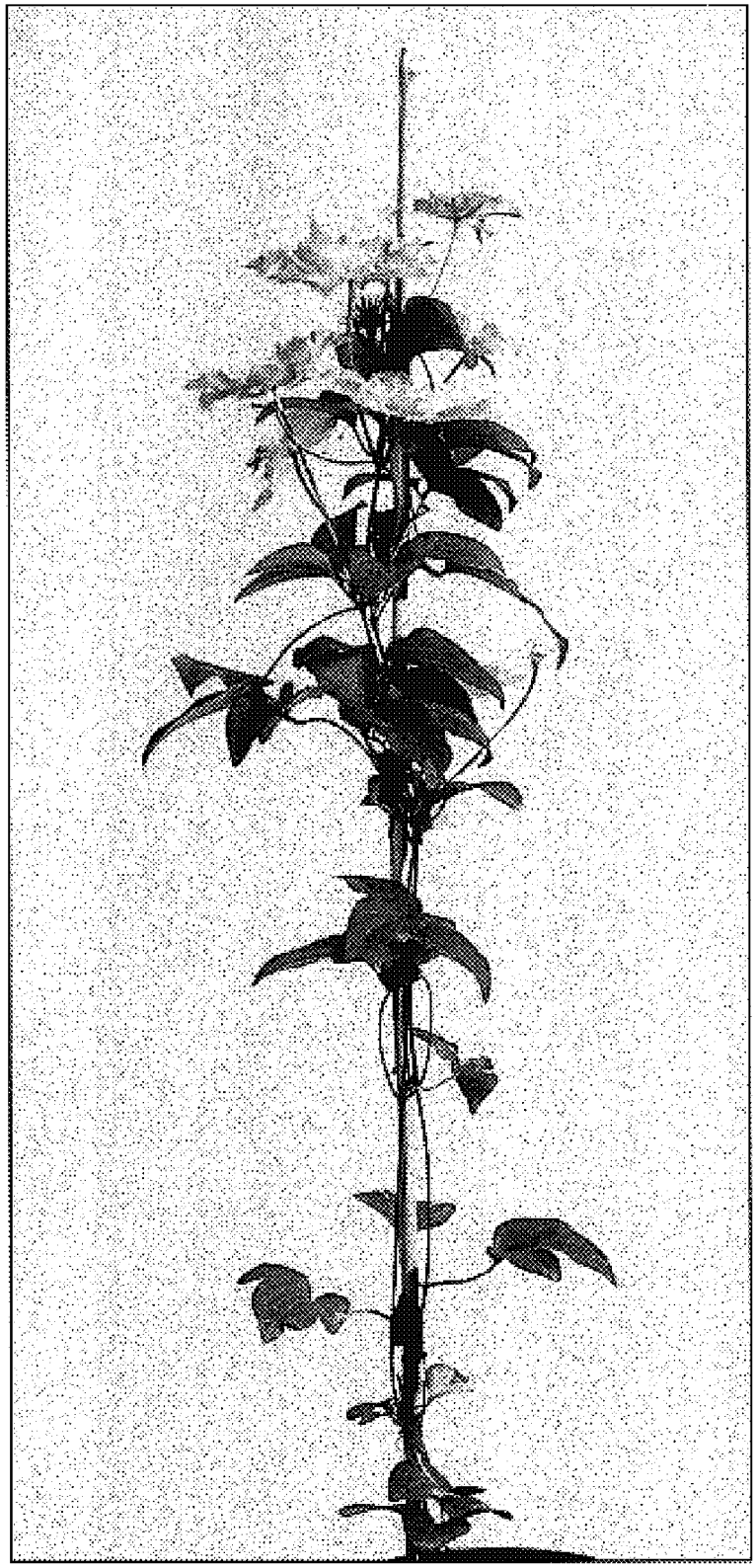

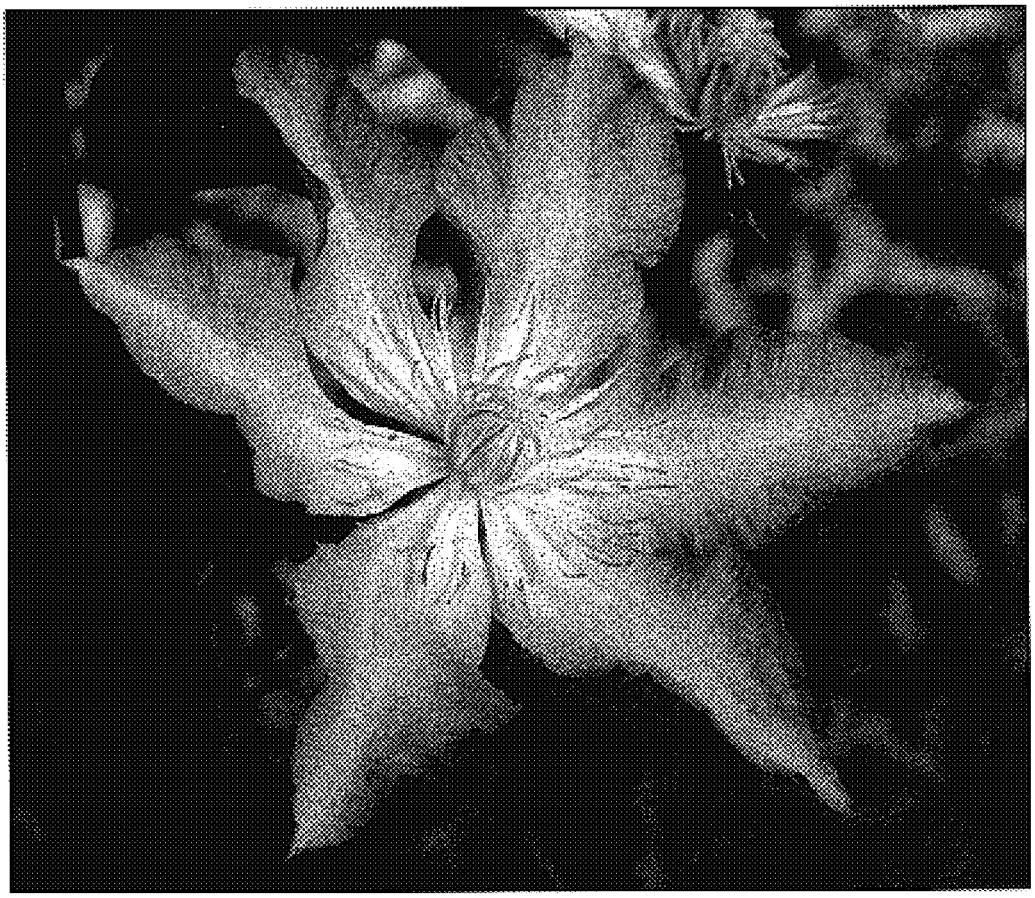
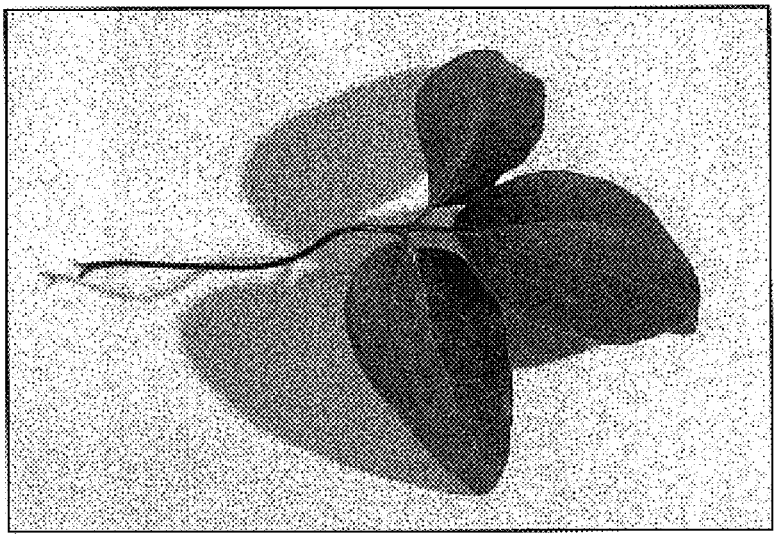

* * * * *